United States Patent [19]

Loper et al.

[11] 3,933,044

[45] Jan. 20, 1976

[54] METHOD AND APPARATUS FOR MONITORING TEMPERATURES DURING CATALYTIC REGENERATION

[75] Inventors: D. Roger Loper, Lafayette; Walter E. Fauerso, Richmond, both of Calif.

[73] Assignee: Chevron Research Company, San Francisco, Calif.

[22] Filed: Mar. 15, 1973

[21] Appl. No.: 341,626

[52] U.S. Cl............ 73/355 R; 23/230 A; 23/288 B; 73/340; 73/362.8; 250/334; 250/342; 252/416
[51] Int. Cl.². G01J 5/08; B01J 37/08; G01N 25/48
[58] Field of Search.......... 23/288 B, 288 H, 230 A; 73/340, 362.5, 362.8, 355 R, 355 EM, 349, DIG. 7; 250/334, 342; 252/416; 356/44; 236/15 B

[56] References Cited
UNITED STATES PATENTS

| | | | |
|---|---|---|---|
| 2,022,440 | 11/1935 | Slough | 73/362 R X |
| 2,981,590 | 4/1961 | Parker | 252/416 |
| 3,101,618 | 8/1963 | Hance | 73/355 R X |
| 3,191,035 | 6/1965 | Brumfield et al. | 250/334 |
| 3,350,702 | 10/1967 | Herman | 73/355 R X |
| 3,430,045 | 2/1969 | Bjork et al. | 73/355 R X |
| 3,463,007 | 8/1969 | Jones et al. | 73/355 R |
| 3,501,380 | 3/1970 | Perch | 73/355 R X |
| 3,596,519 | 8/1971 | Blonder et al. | 73/355 R |
| 3,600,947 | 8/1971 | Farabaugh | 73/355 R X |
| 3,821,895 | 7/1974 | Sumikawa et al. | 73/355 R X |

Primary Examiner—Richard C. Queisser
Assistant Examiner—Frederick Shoon
Attorney, Agent, or Firm—R. L. Freeland, Jr.; H. D. Messner

[57] ABSTRACT

Careful and accurate indication of regeneration temperatures of catalysts associated with the refining of hydrocarbons such as occur in catalyst-aided hydrocracking and catalyst-aided reforming processes—in real time—occurs by monitoring the infrared energy, say in a frequency range greater than $300 \times 10^9$, but not more than $10^{15}$ Hz, emitted from a plurality of distributed metallic studs mounted as by welding to the exterior surface of the sidewall of a vessel undergoing catalytic regeneration. The dynamic temperature variation of such energy rays readily indicate regeneration temperatures of the catalyst interior of the vessel. The studs extend through the insulation of the vessel, but do not penetrate its interior. Where the regeneration process is cyclically occurring, not only is there a marked decrease in the time required for regeneration, but there is also better statistical certainty that full regeneration of the catalyst has occurred. Further, real-time thermograms have been found to have surprising value as histograms for prognosticating optimum regeneration conditions.

4 Claims, 12 Drawing Figures

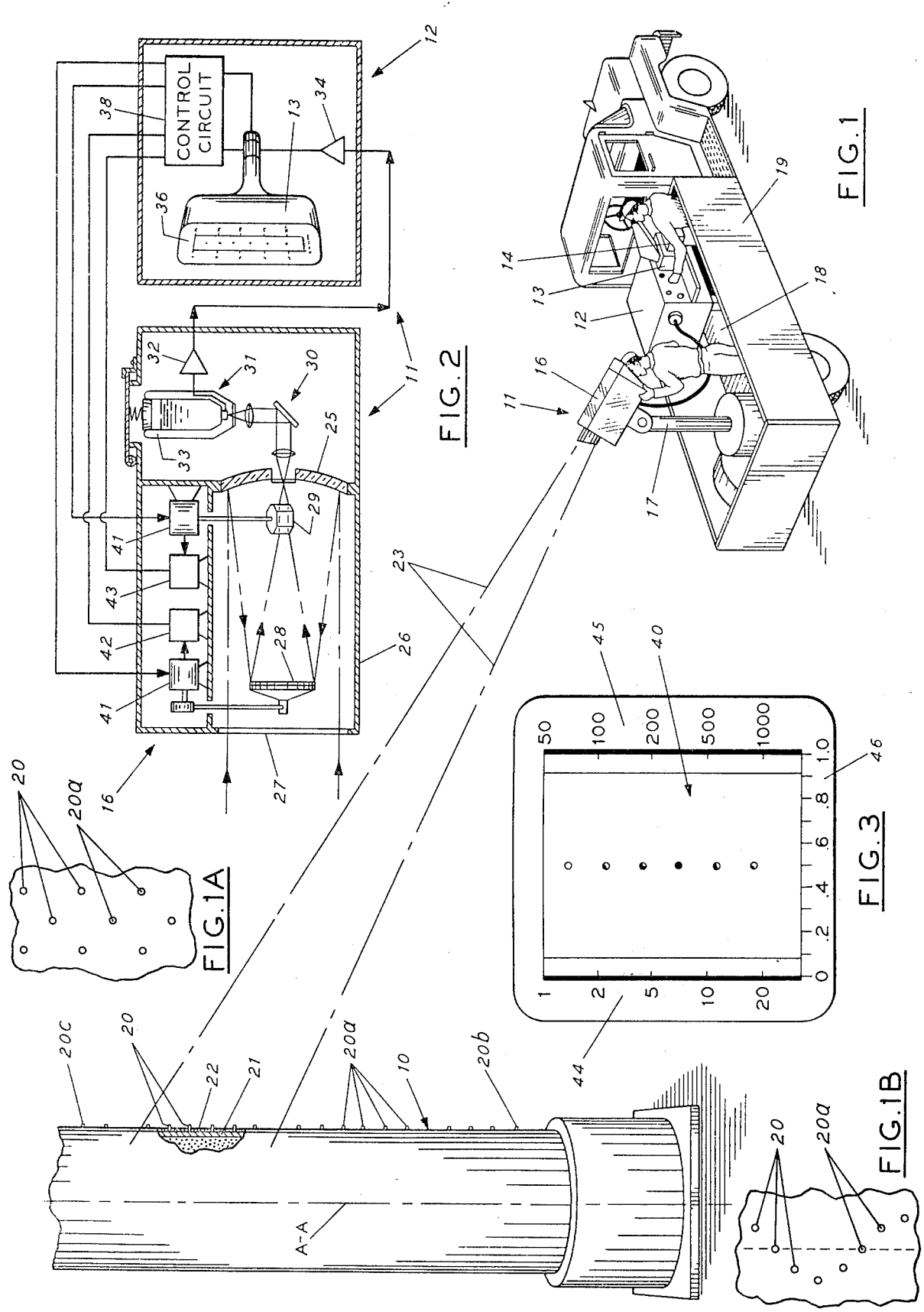

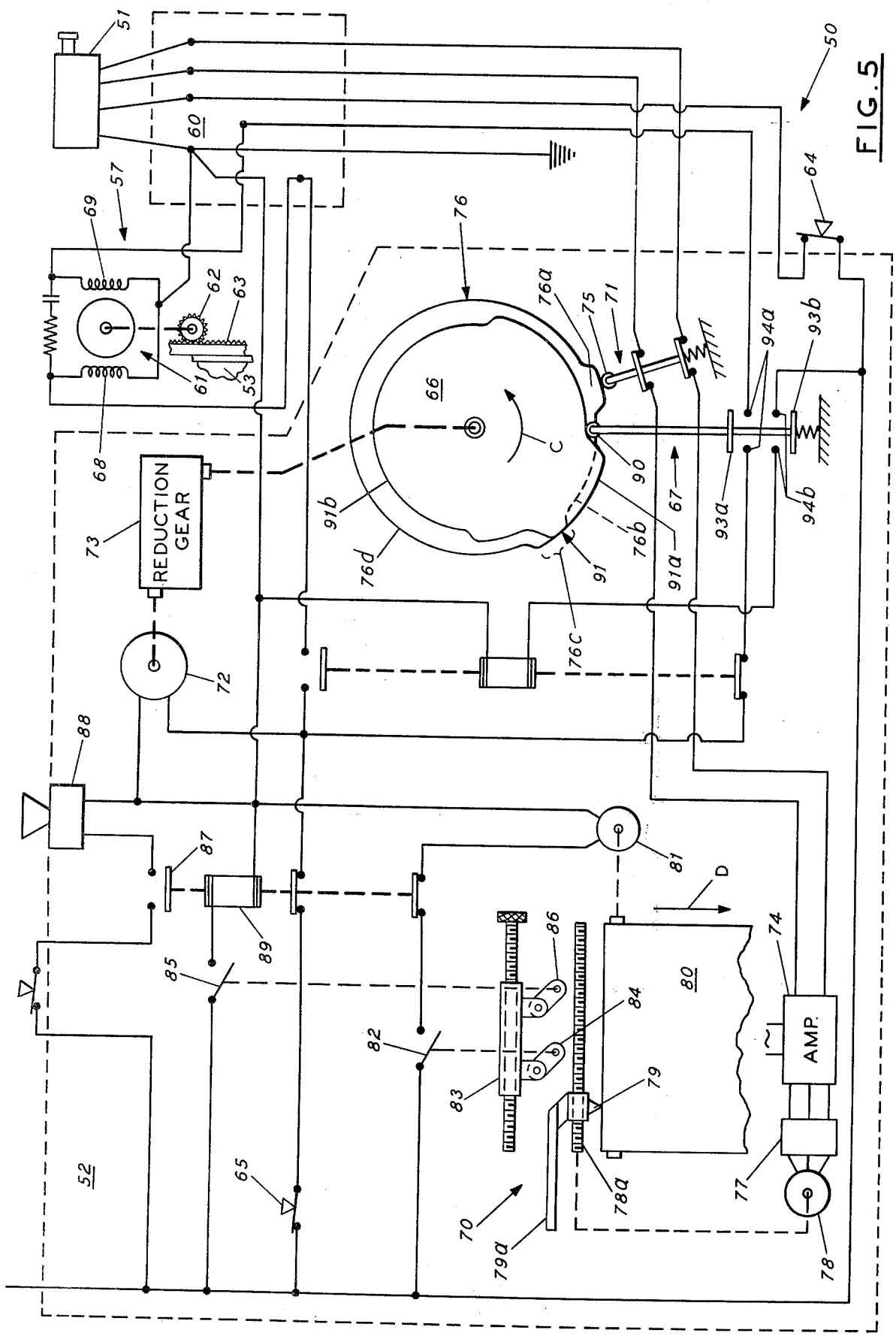

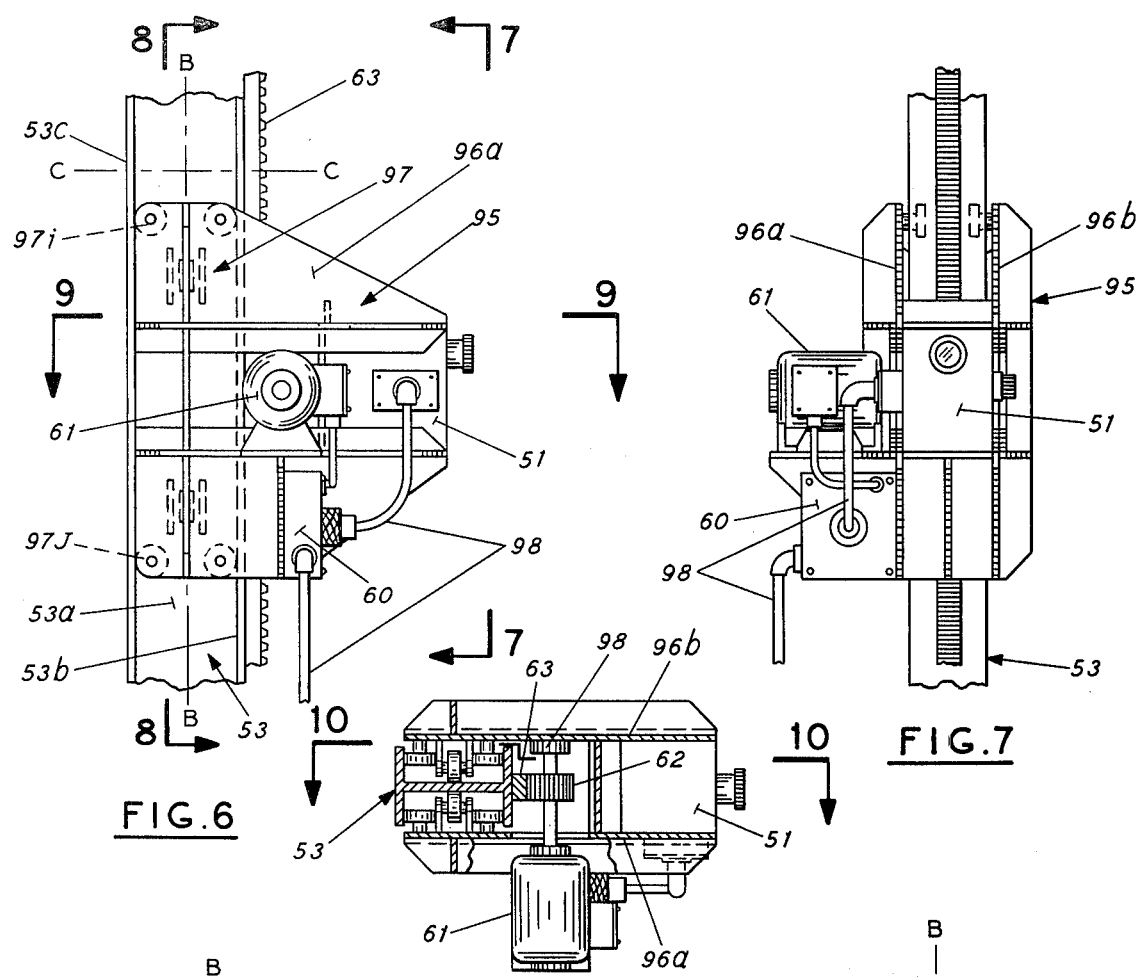
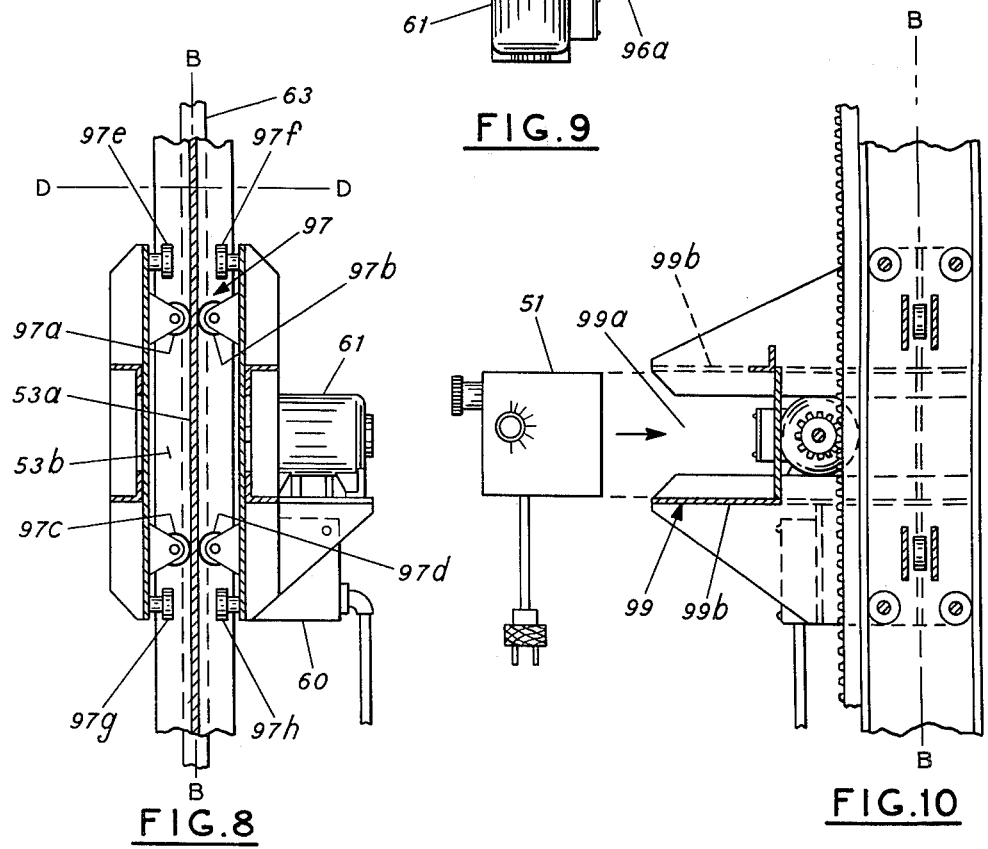

METHOD AND APPARATUS FOR MONITORING TEMPERATURES DURING CATALYTIC REGENERATION

CROSS-REFERENCE TO RELATED APPLICATION

Reference should also be made to a copending application for "METHOD AND APPARATUS FOR MONITORING TEMPERATURES DURING CATALYTIC REGENERATION FROM A CONTINUOUSLY MOVING INFRARED SCANNING AND DETECTION UNIT FIXEDLY MOUNTED ABOARD AN AIRCRAFT," filed concurrently with the present application on Mar. 15, 1973, Ser. No. 341,649, in the name of Armand C. Comfort, assigned to the assignee of the present application.

FIELD OF THE INVENTION

This invention relates to a method and apparatus for improving the efficiency of catalyst regeneration associated with the refining of hydrocarbons such as occur in catalyst-aided hydrocracking and catalyst-aided reforming processes. More particularly, this invention relates to an infrared scanning method and apparatus for improving catalytic regeneration in such refining operations through careful monitoring of temperatures within vessels associated with the regeneration process.

SUMMARY OF THE INVENTION

In accordance with method aspects of the present invention, accurate indication of regeneration temperatures of catalysts—in real time—instantaneously occurs by monitoring the infrared energy, say in a frequency range greater than $300 \times 10^9$, but not more than $10^{15}$ Hz, emitted from a plurality of distributed metallic studs mounted as by welding to the exterior surface of the sidewall of a vessel undergoing catalytic regeneration. The dynamic temperature variations of such energy rays readily indicate regeneration temperatures of the catalyst interior of the vessel. The studs extend through the insulation of the vessel, but do not penetrate its interior. Where the regeneration process is cyclically occurring, not only is there a marked decrease in the time required for regeneration, but there is also better statistical certainty that full regeneration of the catalyst has occurred. Further, real-time thermograms have been found to have surprising value as histograms for prognosticating optimum regeneration conditions.

In accordance with apparatus aspects of the present invention, real-time thermograms of the regeneration cycle are provided by an infrared scanning and detection unit mounted to the bed of a pickup truck positioned adjacent to the vessel associated with the regeneration process. The scanning and detection unit includes a camera unit for detecting infrared energy emitted from studs welded to the vessel. As infrared radiation is emitted from the studs, the camera unit detects the energy by means of an infrared detector. The detector converts the infrared signal to electrical signals. The latter, after amplification, can be used to control the beam of the cathode-ray tube mounted within a console also carried on the pickup bed. The sweep of the cathode-ray tube is matched to that of the camera, so that the resulting image is readily structured to yield both temperature and locational information related to the regeneration process. A recording camera attached adjacent to the screen of the cathode-ray tube photographs the image of the screen. In this way, important regeneration parameters, viz. temperatures, are recorded for future study. Also, by adjusting the temperature sensitivity of the infrared camera unit, wave-front catalyst temperature differences can be indicated over a rather wide range of operating temperatures, say from 1° to 1,360°F.

Still further in accordance with apparatus aspects of the present invention, one or more infrared scanning units can also be mounted to a vertically extending support rail permanently located adjacent to, but horizontally spaced from, a vessel associated with a continuously occurring regeneration process. A column of studs welded to the vessel defines a vertical plane passing through the rail and scanning unit. The camera unit is mounted on an H-frame support which, in turn, is movably mounted to the rail. A drive unit is electrically connected to a control and detection circuit permanently affixed at the base of the rail, the circuit automatically monitoring and initiating operations through a series of switches and other circuit elements, so as to control rectilinear movement of the scanning unit along the rail as a function of time. As a result, a series of thermograms can be generated from different viewing stations adjacent to the vessel undergoing regeneration.

BACKGROUND OF THE INVENTION

Catalytic processes play a heavy role in refining carbonaceous materials. Likewise, regeneration of the involved catalyst logically occupies a correspondingly large amount of a process engineer's time and efforts. For example, in the conversion of high-boiling, non-gasoline hydrocarbons into lower-boiling gasoline components, the catalyst-aided process steps of treating, decomposition, fractionation, gasoline stabilization and absorption polymerization requires, for the most part, cyclic or occasional regeneration of the involved catalysts. See for example, Kirk-Othmer, *Encyclopedia of Chemical Technology*, 2nd Edition, Vol. 15, "Petroleum (Refinery Processes)," page 15 et seq.

Catalysts are usually classified by function--fixed bed, movable bed, or fluid bed--and by process conditions, three typical process examples being set forth below to better illustrate the nature of atalyst-aided processes in general and regeneration techniques in particular:

1. Early catalytic crackers were usually of the fixed-bed type, but today most catalytic cracking is carried out in moving or fluid beds. Regeneration temperatures and pressures in moving and fluid beds are usually in the ranges of 1,000°–1,210°F. and 8–30 psig, respectively;

2. Modern hydrocrackers employed in hydrocracking (an efficient, low-temperature catalytic method for converting refractory middle-boiling or residue streams to high-octane gasoline or jet fuel, etc.) use fixed-bed processing for the most part. After hydrogen has been mixed with the feed, the mixture is heated and contacted with a catalyst in a separate fixed-bed reactor at specified hydrogen partial pressures. Regeneration pressures and temperatures of the catalysts are usually within the ranges of 400°–800°F. and 10–2000 psig, respectively; and 3. Modern catalytic reformers associated with catalytic reforming (upgrading naphthas into high-grade components for fuel blending or petroleum usage in which molecules are rearranged to give a higher antiknock quality at the expense of yield) also employ fixed beds in the main, i.e., it is estimated that less than 5% of U.S. reforming capacity utilizes fluid- or moving-bed processes. Temperatures and pressures for regeneration of catalysts involved in reforming are in the ranges of 800°–1500°F. and 200–400 psig, respectively.

In controlling regeneration temperature and pressure conditions within the above processes, it has been found that the aforementioned variables are usually not monitorable in a direct fashion. Safe engineering practices dictate against the use of internal sensors, for the most part, because associated control and energization elements must in some manner penetrate the sidewalls of the vessels undergoing regeneration. Instead, temperatures and pressures of associated regeneration fluids flowing relative to the vessel are monitored, and temperatures of the catalytic regeneration process are inferred from temperature and pressure values measured at external sensing locations.

Although infrared scanning techniques have been used in many refinery applications, such applications of which I am aware have been limited in scope and function. Moreover, such techniques were thought not to have the capability of monitoring regeneration processes to which the present invention is directed to the extent of detecting and differentiating adjacent temperature stations within catalyst beds of vessels undergoing regeneration, since such vessels are for the most part heavily clad with insulation, so that metallic sidewalls (which could be associated with interim regeneration temperature characteristics) are almost totally hidden from camera view.

OBJECT OF THE INVENTION

An object of the present invention is the provision of a novel method and apparatus for improving efficiency of regeneration of catalysts employed in catalytic processes in general and catalytic hydrocracking and reforming processes in particular, through the careful infrared monitoring of temperatures associated with catalytic regeneration within reactors or within separate regeneration facilities of vessels associated with the regeneration process.

Further objects and features of the present invention will become more apparent to those skilled in the art in the following detailed description of preferred embodiments, wherein:

FIG. 1 is a perspective view of a vessel undergoing catalytic regeneration, such vessel being monitored by means of an infrared scanning and detection unit mounted on a pickup truck bed, such unit detecting infrared energy emitted from a plurality of metallic studs mounted to the sidewall of the vessel extending through the insulation thereof;

FIGS. 1A and 1B are detailed drawings of alternate metallic stud patterns positioned on the side wall of the vessel of FIG. 1;

FIG. 2 is a schematic diagram of the infrared scanning and detection unit of FIG. 1;

FIG. 3 is a thermogram produced by the infrared scanning and detection unit of FIG. 2, in which temperatures associated with the plurality of studs in FIG. 1 are indicated;

FIG. 5 is a schematic diagram of the scanning and detection unit of FIG. 4;

FIG. 6 is a side elevation, slightly enlarged of the scanning unit of FIG. 4;

FIG. 7 is a sectional view of the scanning unit of FIG. , taken along line 7—7 of FIG. 6;

Figure 4:
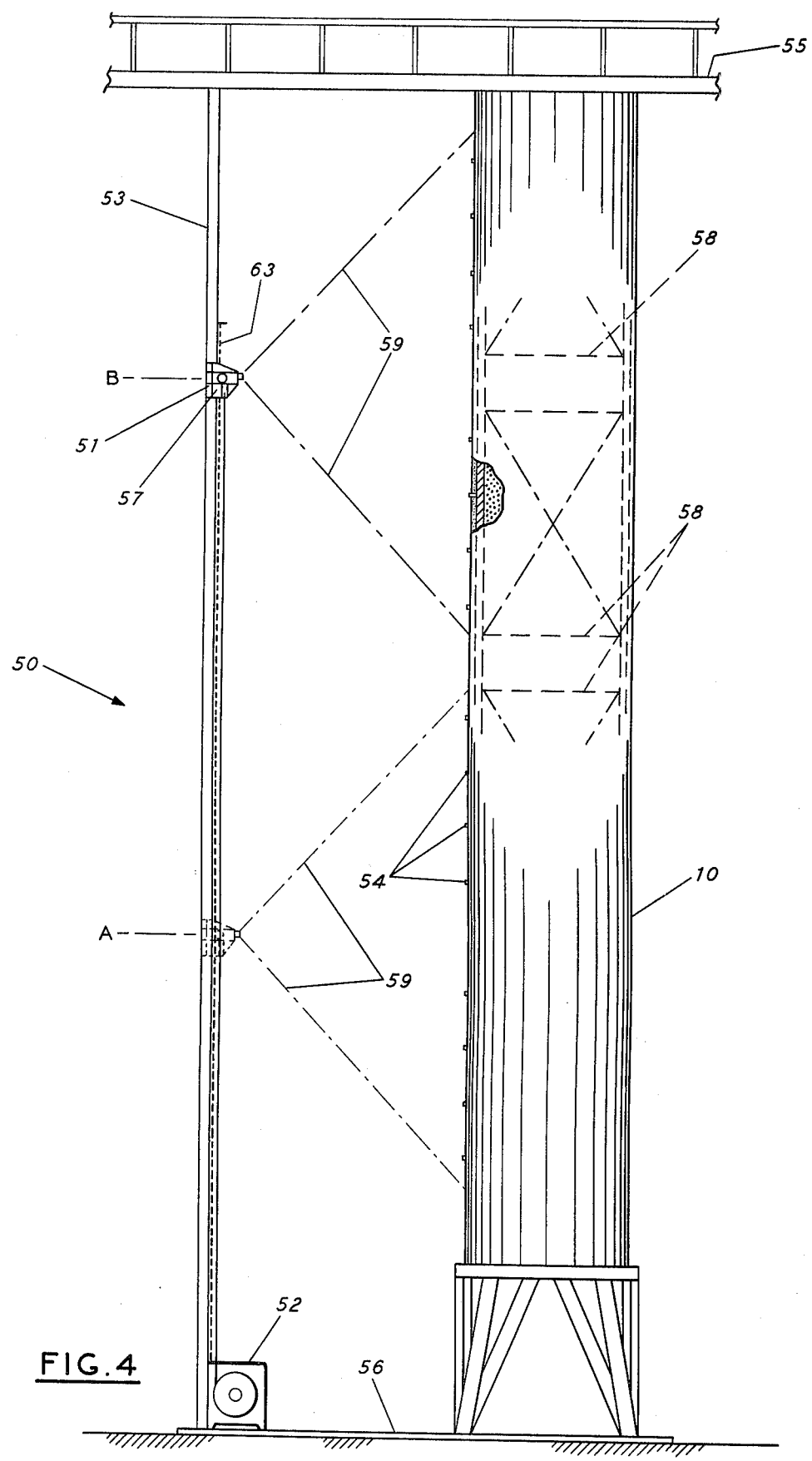
FIG. 4 is a side elevation of another vessel undergoing catalytic regeneration in which fixed-catalyst-bed temperatures are automatically monitored by means of a cyclically repeating infrared scanning and detection unit, such unit including a vertical traveling infrared camera unit, movable along an upright support rail extending parallel to the vessel to be monitored.

FIGS. 8 and 9 are sections taken along 8—8 and 9—9, respectively, of FIG. 6; and FIG. 10 is yet another section, taken along line 10—10 of FIG. 9.

DETAILED DESCRIPTION OF THE INVENTION

Referring now to FIG. 1, temperatures interior of vessel 10 undergoing catalytic regeneration are quickly and easily indicated by infrared scanning and detection unit 11. Vessel 10 is associated with the refining of hydrocarbons in general, and in hydrocracking and reforming processes in particular. Since the temperatures interior of vessel 10 are indicative of the catalytic regeneration process and such temperatures dynamically vary the function of catalyst position within the vessel, scanning and detection unit 11 must be able to dynamically detect slight temperature variations from position to position along the vertical extent of vessel 10.

In accordance with the present invention, scanning and detection unit 11 provides the required temperature resolution in the vertical plane of vessel 10, and includes control console 12. Console 12 comprises cathode-ray tube display unit 13 and recording camera 14. Briefly, in operation, images at cathode-ray tube display unit 13 are produced at a stationary viewing station by infrared camera 16 mounted on pedestal 17, journaled in turn at bed 18 of truck 19 in position adjacent to console 12. The vertical extent of camera image, and hence to available vessel scanning region, is variable by movement of truck 19 so as to allow infrared camera 16 to scan the entire vessel, say when vessel 10 is used as a separate regeneration facility in a fluid-bed or moving-bed regeneration process, or scan only a section of vessel 10, say when the vessel is associated with a fixed-bed process.

The temperatures interior of the vessel are indicated by series of studs 20. The shape of studs 20 can vary, but are preferably of a circular cross-section for ease of manufacture. In accordance with the present invention, studs 20 are mounted as by welding to the exterior of sidewall 21 of vessel 10, and protrude through insulation 22 so that ends 20a are visible to the naked eyes of the human operators of scanning and detection unit 11.

Orientation of studs 20 varies in a preselected manner —say along a vertical, discontinuous column coextensive with insulation 22, having one "edge" thereof defined by a straight vertical line intersecting unattached ends 20a of studs 20, but terminating at ends coincident with base stud 20b and overhead stud 20c. Thus, it is apparent that the studs themselves define a series of exterior, equidistant locations coincident with a common vertical plane passing through both stud ends 20a and axis of symmetry A—A of vessel 10.

Associated with the aforementioned series of exterior locations is a set of imaginary, equidistant temperature stations interior of vessel 10, not shown. Such set of imaginary stations also lies in the aforementioned vertical plane and intersects that plane along a vertical line that is tangent to the interior surface of sidewall 21.

The interior stations of each set are also laterally offset from corresponding exterior locations by a distance equal to at least the thickness of sidewall 21 and the thickness of insulation 22. In addition, if the length of each stud is above the exterior surface of insulation 22, such incremental length must also be added to obtain the aforementioned lateral offset distance. But if the stud height is coincidental with the outer surface of insulation 22, it is apparent that the previously mentioned plane of reference will intersect stud ends 20a along a vertical line that also would be tangent to the outer surface of insulation 22.

Study patterns other than the aforementioned discontinuous column arrangement of FIG. 1 could also be used. For example, studs 20 can be oriented in a series of vertically extending, cyclically repeating 5-spot patterns. See FIG. 1A. Each 5-spot pattern would be positioned on an imaginary curve section, such sections intersecting outer end surfaces 20a of studs 20 and having an axis of formation coincident with the axis of symmetry A—A of vessel 10. As a still further modification of the stud pattern of FIG. 1, it is also contemplated that studs 20 could be oriented in a series of sinusoidal patterns having as a principal reference axis a vertical line tangent with the outer surface of insulation 22 of vessel 10. See FIG. 1B. Note that in the aforementioned sinusoidal pattern, remote ends 20a of the studs would be positioned in imaginary curve section having an axis of formation also oincident with the axis of symmetry A—A of vessel 10.

It should be apparent that in all of the examles of possible stud patterns described above, studs 20 do not extend interior of sidewall 21 of vessel 10. However, because of the solid heat transfer characteristics of the metal of the studs, there is still sufficient proximity of location adjacent to temperature stations interior of the vessel during regeneration that catalyst temperature can be clearly indicated by the surface temperatures of remote ends 20a of each stud 20. Moreover, since the temperatures can be most easily detected if remote ends 20a of the studs are visible to the human eye, as previously mentioned, the length of each stud is accordingly preferably at least equal to the thickness of insulation 22.

While the spacing and number of studs 20 are dependent upon stud pattern, as described above, other factors of interest should be mentioned, including bed length and heat transfer characteristics of sidewall 21 and studs 20. As a minimum, the stud number per unit length of vessel must be sufficient to insure full top-to-bottom temperature information of each catalyst bed during each regeneration cycle. I.e., the vertical extent of the image of infrared camera unit 16, say as indicated by phantom lines 23, must be sufficient to indicate full top-to-bottom regeneration temperature variations as a function of time.

The process of mounting studs 20 to vessel 10 is straightforward: after each stud has been correctly positioned in any of the aforementioned patterns, welding of the studs is carried out using conventional welding techniques. Vessel 10 can then be stress-relieved.

FIG. 2 illustrates operation of scanning and detection unit 11 of the present invention in more detail.

As indicated, infrared camera unit 16 includes focusing spherical mirror 25. Mirror 25 is seen to be centrally disposed within housing 26. Infrared radiation enters through optic window 27 and is focused by mirror 25. The camera scans the total viewable space in two ways: vertically with oscillating mirror 28, and horizontally with multisided prism 29. The resulting scan radiation then propagates through lens system 30 to infrared detector 31. Infrared detector 31 converts the radiation signals to electrical video signals using a photovoltaic effect, as provided by, say, an indium antimonide photovoltaic detector. Liquid nitrogen housed within cooling system 33 provides required cooling of detector 31.

After amplification by amplifier 32, the signals from detector 31 enter console 12 and are again amplified, say by amplifier 34. The amplified signal is then used as a modulating signal for cathode-ray tube display unit 13. Cathode-ray tube display unit 13 is seen to have cathode-ray-tube screen 36. The intensity of the image provided at screen 36 is, of course, a function of the variation in modulating signal provided by amplifier 34. The resulting flickering image (intensity modulation) is photographed by recording camera 14 (see FIG. 1) in time and geometric synchronism with the raster sweep of camera unit 16 over the viewable space of interest. Control circuit 38 connected between cathode-ray tube display unit 13 and infrared camera unit 16 controls the entire infrared scanning and detection operations, as explained in detail below.

The principle of operation of scanning and detection unit 11 is relatively simple. Hot objects, such as studs 20 mounted to vessel 10 of FIG. 1, give off higher frequencies of infrared rays than do other objects. In detecting the rays, say in an infrared frequency range greater than $300 \times 10^9$, but not more than $10^{15}$ Hz, primary optics window 27 and spherical mirror 25 form an image of the object at prism 29. With regard to horizontal resolution of the object, assume prism 29 is an 8-sided prism, and is rotating at about 200 revolutions per second. Accordingly, it follows that 1600 horizontal lines of identifying information could be scanned each second of operation of camera unit 16. Likewise, if each scan frame on screen 36 contains 100 vertical lines, then 16 frames of information are produced each second of camera operation. With regard to temperature resolution, such values are usually determined by comparing the object's infrared radiation to that of its surrounding background radiation or to that of a reference source, as expressed in the following equation:

$$P = \epsilon \sigma T^4 / \pi \qquad (1)$$

wherein:

$T$ is the absolute temperature in degrees Kelvin;

$\epsilon$ is the emissivity of the surface of the plane; and $\sigma$ is the Stefan Boltzmann constant of $5.6697 \times 10^{-8}$ watts/$M^{2\circ}K^{-4}$.

The video signal derived from a scene based on the difference in power being radiated from different areas of the scene may be expressed by taking the partial derivative of equation (1) above with respect to temperature, $T$, and emissivity, $\epsilon$.

$$\Delta P_T = \frac{4\epsilon \sigma T^3}{\pi} \Delta T + \frac{\sigma T^4}{\pi} \qquad (2)$$

Emissivity of the object may be considered to be a constant equal to unity, with equation (2) becoming:

$$\Delta P = \frac{4\sigma T^3}{\pi} \Delta T \qquad (3)$$

with $$\Delta T = (T_2 - T_1)$$

in which the power change ($\Delta P$) from one object has an emissivity of unity ($\epsilon = 1$) and a temperature $T_1$, as compared to that of a second object with an emissivity of 1 ($\epsilon = 1$) and a temperature of $T_2$.

Of course, the ratio of horizontal and vertical scanning frequencies of the final image of the objects can be altered, if desired. I.e., the line raster can move slowly in a vertical direction, if need be. Thus, the photograph of screen 36, taken with an exposure time of 0.5 seconds or longer, will have superimposed upon itself several frames of the same viewable space, so that line pattern of the moving images on the screen is not noticeable. The resulting multiframe photograph is referred to as a histogram. It should be apparent that the number of superimposed frames per histogram can be varied. By increasing the number, for example, a degree of noise immunity may also be achieved. In this regard, it should be noted that sophistocated statistical techniques may also be used in determining the threshold number. Furthermore, techniques related to the classical problem of image enhancement and image detection are, of course, also available for inclusion with the apparatus of the present invention. Of particular interest in this regard are techniques using the ditigal computer, many of which are detailed in the book "Computer Techniques in Image Processing," Harry C. Andrews, Academic Press (1970).

Timing synchronization between control circuit 38, cathode-ray tube display unit 13 and camera unit 16 can be critical. Not only must control circuit 38 provide for control of the contrast and brightness of cathode-ray tube display unit 13 (contrast being variable as a function of temperature range; brightness being variable as a function of temperature level), but it also must coordinate the sweep of camera unit 16 to that of the display unit. In this regard, as indicated in FIG. 2, drive means 41 is mechanically attached to both mirror 28 and prism 29. Note also that synchronization sweep signals are generated by the interaction of driver means 41 with photocell circuits 42 and 43 and pass through circuit 38 to control operation of cathode-ray tube display unit 13.

Within each field of view of camera 16, the intensity of images (detected frequency) can also be compared, visually, with thermograms of objects of known temperatures, so as to predict the temperature of the images at screen 36. However, with regard to the use of camera 16 to measure the temperatures interior of vessel 10 of FIG. 1, it should be recalled that the heat transfer characteristics of each catalyst bed of the vessel vary rapidly with time and location. Hence, the frequencies of scan of camera 16 must be high enough to provide for such indications as a function of time throughout each regeneration cycle. In this regard, it has been found that thermograms 40 can be generated rapidly enough to provide the required information to optimize the regeneration process, if camera 16 is provided with the aforementioned horizontal and vertical scanning characteristics.

FIG. 3 illustrates a typical thermogram 40 in more detail. As indicated, the temperature differences between the images of the studs attached to the vessel undergoing regeneration appear—in real time—as a black-and-white image. These images appear as flickering lines upon screen 36 of cathode-ray tube display unit 13 of FIG. 2 in time and geometric synchronism with the sweep of camera unit 16. In that way, the resulting images effectively depict the studs in this true geographic perspective with respect to the scanning station. Sensitivity of each resulting thermogram 40 is indicated by scales 44 and 45 placed to the left and right sides of the thermogram as viewed in FIG. 3 (gradation: 1–1000). A gray scale is presented at the bottom of the thermogram at 46 and represents a scale in which a shade of grey equals $\sqrt{2}$ times the intensity of the next preceding level. Not only are visual methods available to determine temperature levels of each thermogram 40, but also automatic machine comparison techniques can be used to analyze the informational content of each thermogram 40. For example, a digital comparison circuit (not shown), say located internally of control circuit 38, could be used to automatically analyze a series of thermograms without need for human intervention, such circuit using a binary scale (ONE and ZERO) in which the ONE state is a black dot and the ZERO state is a white dot after analog-to-digital conversion of the signals from detector 31 has occurred. Each ONE or ZERO state can be determined over a selected range of temperatures. Shades between the ZERO and ONE states reflect gradations of temperature levels within the selected range. Also, the resulting thermograms can be compared—line by line—with previously obtained thermograms which represent instances in the regeneration cycle in which exceptional response levels occur. In that way, optimization of the currently occurring regeneration process can be obtained.

Modification

FIG. 4 illustrates a modification of scanning and detection unit 11 of FIG. 1 for viewing vessel 10 from a series of cyclically repeating view stations, i.e., say from view stations A and B of FIG. 4.

As shown, reference numeral 50 indicates the modified scanning and detection unit in detail, scanning and detection unit 50 being seen to include camera unit 51 movable along support rail 53 and detection and control circuit 52 fixed in position at the base of rail 53. Rail 53 is parallel but laterally offset from a plurality of metallic studs 54 of vessel 10 and is held at its ends by catwalk 55 and by base plate 56. Movement of the camera unit along rail 53 is provided by a drive unit, generally indicated 57.

In operation, as set point conditions occur, as indicated by control unit 52 as explained hereinafter, camera unit 51—on command—moves in a vertical direction along rail 53. When camera unit 51 is at scan station A or B, however, movement of the camera unit ceases and the camera is activated to detect the emission of infrared energy from studs 54. In that way, temperatures within associated sets of locations within fixed catalyst bed 58 interior of vessel 10 can be determined in the fashion as previously described with reference to FIG. 1. Note that each scanning station is fixed at a selected but different height above base 56. Thus, at each of stations A or B, the focal lengths of camera unit 51 can be accurately controlled so that the total field of view (as defined by phantom lines 59 of camera 51) is equal to at least the vertical extent of each catalyst bed 58. In that way, temperature rises occurring within each catalyst bed 58 can be easily indicated and recorded as a function of time.

FIG. 5 schematically illustrates operation of modified scanning and detection unit 50 in more detail. As schematically illustrated, camera unit 51 and junction box 60 move along rail 53 by operation of driving unit 57. Driving unit 57 includes motor 61. Motor 61 has a shaft connected through pinion gear 62 to rack 63 mounted to rail 53. Windings 68 and 69 of motor 61 are selectively activated to control rectilinear movement of camera unit 16 in the manner described below. Support for camera unit 51 and junction box 60 is also described in detail below.

Motor 61 can be appropriately connected to a source of energy through operation of timing wheel 66 in conjunction with double-elemented control switch 67 forming elements of control unit 52. Briefly, in the ON state, double -elemented switch 67 allows current flow to either winding 68 or 69 of motor 61. Rotation of the shaft of motor 61 is either in a clockwise or a counter-clockwise direction, such rotation being converted through pinion gear 62 to rectilinear movement of camera unit 51. Rectilinear movement is either in an upward direction from station A to station B or in a downward direction from station B to station A, depending on which switch element 93a or 93b of switch 67 is connected, as explained below.

Control unit 52 also is seen to include recorder 70 alternatively connected to camera unit 51 through cooperation of a second double-elemented infrared control switch 71. Infrared control switch 71 is placed in cooperative contact with timing wheel 66 at a peripheral location adjacent to that of double-elemented switch 67. Briefly, in operation, timing wheel 66 is seen to be connected to drive motor 72 through gear reducer 73. Cooperative rotation of timing wheel 66 and switches 67 and 71 changes the switching status of the latter so as to provide selected control of drive unit 57 and camera unit 51 as follows:

i. drive unit 57 and camera unit 51 stationary at station A, camera unit 51 is in an ON state;

ii. drive unit 57 and camera unit 51 in rectilinear motion in a first direction traveling from station A to station B, camera unit 51 is an OFF state;

iii. drive unit 57 and camera unit 51 stationary at station B, camera unit 51 is in an ON state;

iv. drive unit 57 and camera unit 51 in reverse rectilinear movement between station B and station A, camera unit 51 is an OFF state.

Operative steps i–iv will now be described in more detail with reference to FIG. 5.

Step (i): Assume switches 64 and 65 have been activated. Timing wheel 66 is in rotation in the direction of arrow C through operation of drive motor 72 and gear reducer 73. Roller 75 of double-elemented infrared switch 71 is placed in rolling contact with node 76a of timing rack 76 of timing wheel 66. Under such conditions, electrical signals provided by camera unit 51 can be applied, after amplification by amplifier 74 into measuring unit 77 of recording unit 70. Signals from measuring circuit 77 are converted through balancing motor 78 to rotational movement of shaft 78a connected to pen 79 of recording unit 70. Pen 79 moves laterally across chart 80 as a function of signal intensity from camera unit 51. When activated, chart motor 81 is seen to advance chart 80 in direction D. However, chart motor 81 is not initially activated. Only when limit switch 82 is tripped (through interaction of bar 79a of pin 79 and lever arm 84 of mechanical limiter 83) does chart motor 81 become operative. Chart motor 81 continues to operate, once activated.

It should be noted that mechanical limiter 83 is also provided with second lever arm 86. When activated by lever arm 86, contact switch 85 is seen to be tripped, which in turn activates relay 89. Relay 89 includes plunger contact 87, which, when activated, connects horn 88 with source of energy (not shown). It should be apparent that relay 89 allows horn 88 to sound a warning to alert operators within the area that a maximum set point temperature of regeneration has been reached interior of vessel 10. Simultaneously, as relay 89 is operative, there is deactivation of the following: motor 72, connected to timing wheel 66 and chart motor 81. It should also be apparent that when horn 88 is activated, camera unit 51 remains fixed at either station A or B so that the overheated catalytic bed of the vessel can be readily identified.

Step (ii): As infrared controls switch 71 is opened by its roller 75 entering dwell regions 76b of track 76 of timing wheel 66, control switch 67 is activated: roller 90 contacts node 91a of track 91. When this occurs, switch element 93a is placed across contact points 94a. Thus, travel motor 61 becomes energized.

As motor 61 rotates, pinion gear 62 likewise rotates and is caused to travel with respect to rack 63. Since pinion gear 62 and motor 61 are mechanically linked to camera unit 51, the latter is caused to travel from station A to station B.

Since infrared switch 71 is inactive during this time, pen 79 of recording unit 70 falls to a level which places switch 82, controlled by mechanical limiter 83, in an inactive state. Such inactive state in turn deactivates chart motor 81.

Step (iii): With drive unit 57 positioned at station B, camera unit 51 operates in the same manner as previously described with reference to step (i) above. That is, camera unit 51 is operative to provide infrared signals at recording unit 70 through closure of infrared switch 71, i.e., by placement of its roller 75 in rolling contact with node 76c of timing track 76 of timing motor 66.

Step (iv): As infrared control switch 71 is again opened, i.e., opened by its roller 75 entering a second dwell region 76d, roller 90 of control switch 67 enters reversing dwell section 91b on timing track 91. It is apparent that as a result of roller 90 entering reversing dwell section 91b, switch element 93b of switch 67 is placed across contact points 94b. Travel motor 61 becomes energized; however, such energization is in a reverse mode to that previously described, since the direction of current flow relative to windings 68 and 69 is reversed. This causes, in turn, reverse rotation of pinion gear 62 relative to rack 63, which causes travel of camera unit 51 from station B to station A. Camera unit 51 and drive unit 57 return to station A, at which time a second scanning cycle can be initiated, if desired.

FIG. 6, along with detail drawings FIGS. 7, 8, 9 and 10, illustrates the manner in which drive unit 57 and camera unit 51 are supported relative to rail 53.

As indicated in FIGS. 6 and 7, camera unit 51 and drive unit 57 are supported by H-frame support 95, having upright sides 96a and 96b. Upright sides 96a and 96b slideably connect to rail 53 and include a cantilevered section (FIG. 6) which extends away from rail 53 so as to form a support region for camera unit 51. At a more central region of H-frame 95, side 96a is also seen in FIG. 7 to provide support for junction box 60 and travel motor 61. Electrical energy is provided to camera unit 51 and to travel motor 61 through cooperative connection of electrical connector 98 to a source of electrical energy within control circuit 52 at the base of support rail 53 (see FIG. 4). Sides 96a and 96b of H-frame 95 also support, at its interior, a series of balance rollers which provide a balance roller unit, generally indicated at 97 in FIG. 6. The purpose of balance roller unit 97 is to prevent rotation of H-frame support 95 relative to rail 53 about axis C—C (FIG. 6) and axis D— D (FIG. 8) while still allowing rectilinear movement of H-frame 95 along axis B—B (FIG. 6).

FIG. 8 illustrates balance roller unit 97 in more detail. In this regard, note that the structure of rail 53 is designed to snuggly accommodate roller unit 97 for the previously expressed purpose of preventing rotation about axes C—C and D—D, but allowing rectilinear movement along axis B—B. In more detail, rail 53 is seen to be a conventional I-beam design such that web section 53a is snuggly positioned between rollers 97a–97d of roller unit 97. While rectilinear travel of H-frame support 95 along the rail is permitted, note that rotation about web section 53a is not allowed. Remaining rollers comprising roller unit 97 prevent rotation about the remaining principal rotation axis C—C of FIG. 6 in the following manner: rollers 97e–97h of FIG. 8 prevent movement of H-frame 95 in the direction of end section 53b of rail 53, while similarly positioned rollers of roller unit 97 (two of which being indicated at 97i and 97j of FIG. 6) prevent movement in the opposite direction, i.e., toward section 53c of rail 53.

FIGS. 9 and 10 illustrate the operation of travel motor 61, pinion gear 62 and rack 63 in more detail. As shown in FIG. 9, travel motor 61 includes shaft 61a journaled at sidewall 96b by bearing 98. At a central region of shaft 61a, pinion gear 62 is affixed. Gear teeth are seen to be in mating contact with rack 63 attached to rail 53. Thus, rotation of motor 61 relative to gear 62 is directly converted into rectilinear travel of H-frame 95 in the direction of axis B—B of FIG. 10. Of course the gear ratio of the rack and pinion gear must be designed such that movement along axis B—B is smooth but stable.

Since it is also desirable in some circumstances to remove camera unit 51 from H-frame 95 so as to effect repair, support frame 99 of FIG. 10 is arranged to have aperture 99a open at one end, through which camera unit 51 can be loaded. Snug contact of camera unit 51 and interior of H-frame 99 is provided by having its sidewalls 99b in snug contact with similarly oriented walls of camera unit 51. A lock (not shown) is used to releasably connect camera unit 51 relative to frame 99.

Although certain embodiments of the present invention have been illustrated and described, the invention is not meant to be limited by those embodiments, but by the scope of the following claims. E.g.: (1 ) rather than use internal-combustion-engine-power truck 19 in the embodiment of FIG. 1, a nonpolluting mode of transportation could be substituted, if desired; and (2) rather than using only two viewing stations, as depicted in the embodiment of FIG. 4, a greater number may be employed in some applications. With regard to (2) above, note that in such multistation viewing there must be sufficient reversing time of drive unit 57 to allow camera unit 51 to move from its position at the last-of-cycle scanning station back to its original position at the first-of-cycle scanning station before the cycle is repeated.

We claim:

1. Apparatus for monitoring the regeneration of a catalyst located within an insualtion-clad vessel involving elevating the temperature interior of said vessel after production of hydrocarbon products such as petrochemicals, gasoline, light fuel oils, and the like, has been terminated, comprising:
  1. a plurality of metallic stud means affixed to the metallic sidewall of said vessel associated with a similarly oriented spatial position interior of said vessel, for defining a true temperature gradient for catalyst regeneration interior of said vessel as said vessel is utilized in a catalyst regeneration operating mode;
  2. an infrared scanning and detection unit responsive to infrared energy in a frequency frange from about $300 \times 10^9$ to $10^{15}$ Hz, for the purpose of detecting said infrared energy emitted from said plurality of stud means during operation of said vessel in said regeneration mode, and displaying said energy as a function of geometric and time variables indicative of the geographic positions of said stud means as viewed from a scanning station exterior of said vessel, said infrared scanning and detection unit including:
    A. infrared camera means for generating electrical signals as a function of detected infrared energy;
    B. means for allowing said infrared camera means (A) to be movably positioned at a series of vertically separated viewing stations along a pathway extending upwardly from ground level, each being horizontally adjacent to a selected group of said stud means of said vessel;
    C. control means fixably positioned relative to said vessel but electrically connected to said motion allowance means (B) and camera means (A) for controlling movement of said camera means (A) along said vertical pathway, said control means also including first cooperative switch means for controlling operation of said camera means (A) to allow detection of said infrared signals at least when said camera means (A) is stationary relative to said vessel at each of said viewing stations;
    D. recording circuit means also fixedly positioned relative to said vessel, but electrically connected to said camera means (A) for recording said electrical signals generated by said camera means (A) due to the detection of infrared energy emitted from said plurality of stud means of said vessel.

2. The apparatus of claim 1 in which said plurality of metallic stud lie in a series of vertically extending, cyclically repeating 5-spot patterns, each pattern positioned on a common curved arcuate section whose axis of formation is common to the axis of symmetry of said vessel.

3. The apparatus of claim 1 in which said plurality of metallic stud means lie in a series of vertically extending, cyclically repeating sinusoidal patterns, each pattern positioned on a common curved arcuate section whose axis of formation is common to the axis of symmetry of said vessel.

4. The apparatus of claim 1 in which said motion allowance means (2) is further characterized by rail means attached to the earth and extending vertically along said vertical pathway offset from said stud means, H-frame support movably mounted on said rail means to which said camera means (1) is fixedly mounted, reversible drive means permanently affixed to said H-frame support means but movably positioned relative to said rail means, said drive means being in circuit with said control means (3) through a second switch means so as to control rectilinear travel of said camera means (1) and said H-frame support means between said series of viewing stations in sequence, along said vertical pathway as well as to reverse rectilinear travel of said camera means (1) and said H-frame support means after said camera means (1) has been located at a last-of-scan station and to return said camera means (1) to a first-of-scan station, where reinitiation of the scanning cycle can occur, if desired.

\* \* \* \* \*